(12) United States Patent
Rudert et al.

(10) Patent No.: US 7,453,563 B2
(45) Date of Patent: Nov. 18, 2008

(54) DEVICE AND METHOD FOR DETECTING SCRATCHES

(75) Inventors: Armin Rudert, Essen (DE); Ulrich Pingel, Marl (DE)

(73) Assignee: Isra Surface Vision GmbH, Herten (DE)

( * ) Notice: Subject to any disclaimer, the term of this patent is extended or adjusted under 35 U.S.C. 154(b) by 0 days.

(21) Appl. No.: 11/578,220

(22) PCT Filed: Feb. 12, 2005

(86) PCT No.: PCT/EP2005/001440

§ 371 (c)(1),
(2), (4) Date: Oct. 11, 2006

(87) PCT Pub. No.: WO2005/116616

PCT Pub. Date: Dec. 8, 2005

(65) Prior Publication Data

US 2007/0252996 A1    Nov. 1, 2007

(30) Foreign Application Priority Data

May 29, 2004   (DE) ....................... 10 2004 026 375

(51) Int. Cl.
*G01N 21/00* (2006.01)

(52) U.S. Cl. ................................. 356/239.1; 356/239.7
(58) Field of Classification Search ....................... None
See application file for complete search history.

(56) References Cited

U.S. PATENT DOCUMENTS 3,814,946 A    6/1974   Takahashi et al.
5,598,262 A *  1/1997   Jutard et al. ............. 356/239.1
5,745,176 A    4/1998   Lebens

FOREIGN PATENT DOCUMENTS

DE         2 261 460      6/1974
DE         693 07 722     6/1997

* cited by examiner

*Primary Examiner*—Michael P Stafira
(74) *Attorney, Agent, or Firm*—Michael J. Striker

(57) ABSTRACT

The invention relates to a device and a corresponding method for detecting scratches on the surface (2) of a material, in particular glass. Said device comprises an illumination unit (3) and a recording unit (4), which register a scanning line (6) on the surface (2) of the material and can be displaced in relation to said surface (2). In order to more accurately identify scratches, the illumination unit (3) comprises at least one light strip (9), which generates parallel light pools transversally to the scanning line (6), said pools being diffuse or quasi-diffuse along the scanning line (6) and preferably at least one light source (16), which generates a diffuse or quasi-diffuse light transversally to the scanning line (6).

16 Claims, 2 Drawing Sheets

DEVICE AND METHOD FOR DETECTING SCRATCHES

CROSS-REFERENCE

The invention described and claimed hereinbelow is also described In PCT/EP 2005/001440, filed on Feb. 12, 2005 and DE 10 2004 026 375.2, filed May 29, 2004. This German Patent Application, whose subject matter is incorporated here by reference, provides the basis for a claim of priority of invention under 35 U.S.C. 119 (a)-(d).

BACKGROUND OF THE INVENTION

The present invention relates to a device for detecting scratches, in particular on a transparent material surface, such as glass, with an illumination device and a reception device which detect a scanning line on the surface of the material and which are displaceable relative to the material surface, and a related method.

Rough scratches on glass are produced by material being removed with a sharp object. When the material is removed, the glass shatters into irregular, small particles from the smooth surface. This results in irregular structures, which scatter light in all directions, regardless of the direction out of which the incident light comes. Rough scratches of this type are referred to as "rub", "abrasion", "scuffing", "ice-like scratches", and the like. In addition, there are other scratches, which are generally finer, which are produced in the glass surface via plastic flowing under the pressure of a very sharp object. These finer scratches have smooth flanks, which reflect light only in a certain direction, and which are classified as "groove", "flute", "hairline", "ridge", or the like. When you look at the glass from a defined direction, the scratch must be illuminated from a certain direction for it to be seen. Since the scratches can have any possible orientation in the glass, a glass surface to be inspected for scratches must be illuminated from all sides, so that all of the scratches can be identified. Since nearly all scratches transition back into themselves when rotated 180°, it is sufficient to illuminate 180° around the glass surface. It is not necessary to illuminate 360° around the glass surface.

It is difficult to attain illumination of this type with curved glass surfaces in particular. A typical example of an application of this is in the detection of scratches in windshields. Since windshields are generally curved spherically, it is necessary to illuminate at least a certain region uniformly from all sides, the region being located around the scanning line of a reception device, e.g., a digital camera, which advantageously extends from top to bottom. In addition, it is not possible to move all regions of a spherically curved windshield past the camera at the same distance. The illumination must therefore have the required properties of diffuse illumination across a certain depth range. In addition, the reception camera must have sufficient depth resolution in order to deliver sharp images of the scratches. The illumination must therefore be adequately bright. To produce contrast that is distinct enough for scratches to be detected, the camera must generally look into a dark light trap. Light enters the camera only when a scratch is illuminated. It must therefore be ensured that neither light directly from the illumination device nor light reflected by the intact material surface enters the camera. This cannot be accomplished using previous sampling and scanning devices, particularly when they are used with curved, e.g., spherically curved, windshields.

Publication U.S. Pat. No. 5,598,262 makes known a method for inspecting transparent material, with which a camera looks through the transparent material and onto a background which is illuminated uniformly with neon tubes, to detect flaws enclosed in the material. To also detect dust particles lying on the surface of the material, the surface of the material facing the camera is illuminated with a lamp which, due to its design, generates parallel light beams, which therefore generates parallel light transversely to the scanning line and diffuse light in the direction of the scanning line.

A method for detecting flaws in a transparent material is described in publication U.S. Pat. No. 3,814,946, with which every side of the surface of the transparent material is illuminated with parallel light transversely to the scanning line and diffuse light in the direction of the scanning line. The surface of the material is observed with a camera; the illumination device located on the side with the camera detects flaws in the surface, and the illumination device located on the side opposite to the side with the camera is used to detect flaws enclosed in the transparent material.

Publication U.S. Pat. No. 5,746,176 describes a design for generating a light beam using several, adjacently positioned LEDs, which generates light which is parallel in one spacial direction and is diffuse in a spacial direction orthogonal thereto.

SUMMARY OF THE INVENTION

The object of the present invention, therefore, is to also enable reliable detection of scratches, e.g., on spherically curved glass panes or other material surfaces.

The illumination device of the present invention includes at least one light strip, which generates parallel light transversely to the scanning line, the light being diffuse or quasi-diffuse in the direction of the scanning line. The illumination device also preferably includes at least one light source which generates diffuse or quasi-diffuse light transversely to the scanning line, which, in particular, strikes the material surface within a certain angular range with the surface normal. As a result, a sufficiently large area around the imagined scanning line on the material surface is illuminated uniformly from all sides due to the fact that the illumination includes, in particular, two different light components, which are oriented essentially orthogonally to each other, with diffuse or quasi-diffuse light. i.e., light that is incident uniformly from essentially all directions along the stated components.

The light from the light strip and the light from the light source therefore each cover an incident light area of approximately 180°, in components which are essentially perpendicular to each other. As a result, a scratch located in the optical range of the reception device (camera) is illuminated with light from all directions, i.e., diffuse and quasi-diffuse light, so that the scratch always generates luminous reflectance in the camera. By specifying angles of incidence of the particular components of the light on the material surface, it is simultaneously ensured that none of the light reflected on the intact surface enters the camera and incorrectly indicates the presence of a scratch or a flaw.

This can be attained particularly easily according to the present invention when the reception device is located in the region of the surface normal of a point on the scanning line. In this case, only light which strikes the surface of the material in the normal direction would be scattered into the camera. This can be prevented via the inventive positioning of the illumination device, however. With an, e.g., spherically curved, material surface, the reception device is not located exactly at the surface normal of a point on the scanning line in every detecting position, due to the curvature. In this case, it makes sense, e.g., to locate the reception device in the region of the surface normal of the center of the curved surface of the material. When curvature is uneven, in particular, it can also make sense to place the reception device in a different position, however.

The illumination device and the reception device are preferably located on one side of the transparent material. Since windshields generally include areas with printing on the inside of the pane, it is necessary to position the camera and the illumination on the outside. This is the only configuration with which scratches in the black areas can be detected from the outside. These areas can also be seen in the installed state; due to the black background, scratches are particularly obvious to someone looking at the vehicle. It is therefore necessary to inspect these areas. If there are no printed areas (e.g., when several side-window panes are involved), it is also possible to illuminate from the inside, with the camera located on the outside, or vice versa.

According to the present invention, the light strip is preferably tilted at an angle to the surface normal of a point on the scanning line such that an area around the scanning line is illuminated. In this arrangement, with the camera located on the same side, the light strip is located next to the camera, thereby ensuring that light cannot enter the camera directly. Due to the reflectance of the light on the surface of the material at an angle of reflection that corresponds to the angle of incidence, light reflected on the smooth surface of the material does not enter the camera, either, with an arrangement of this type.

To generate the parallel light, the light strip can easily include optics which orient the light beams in parallel.

According to the present invention, a diffuser—in particular a lenticular system—can be located downstream to generate the diffuse light in the direction of the scanning line. To blend the emerging light, a matt screen could also be used, although it would result in transmission losses. A lenticular system composed of microcylinder lenses is therefore advantageous, with which the microcylinder lenses distribute the light uniformly, with high transparency.

To further improve the illumination level, it is also possible to provide two light strips, which are preferably located on either side of the surface normal. The camera is then preferably located between the two light strips. It is also possible, according to the present invention, to locate several light strips next to each other, e.g., two light strips each on one side of the reception device (camera), to intensify the illumination. In this case, a design which is symmetrical around the normal plane of the scanning line is particularly advantageous.

With a design which includes several light strips in particular, it can make sense according to the present invention to locate a flap for covering the light strip on the light strip or on each of the light strips. This flap can be folded in front of the light strip temporarily if there is a risk of direct reflectance entering the camera, e.g., due to a particularly strong curvature of the surface of the material. Electrical switching of the lamps can therefore be eliminated. Depending on the type of lamp used, this can result in waiting periods—particularly when the lamp is turned on again—until the lamp has once more reached its operating temperature.

According to the present invention, the light source for generating the diffuse or quasi-diffuse light components in the other direction, transversely to the scanning line in particular, includes a curved mirror, which is curved around the imagined scanning line, e.g., on a circular path along a certain length that preferably extends 180°. By locating the lamp of this light source in a suitable position in the interior region of the mirror, a nearly uniform illumination of the area around the scanning line with light beams can be attained, the direction of which varies by approximately 180°. Quasi-diffuse light is therefore generated with this design. Instead of the mirror, it is also possible according to the present invention to provide a large number of lamps in the second light source, which are located in a nearly semicircular pattern around the scanning line, thereby generating illumination from nearly 180°, i.e., quasi-diffuse light.

Furthermore, according to the present invention, the mirror can be designed at least as a conic section; a section curved nearly 180° is mirrored on the inside of the cone. Due to a shape of this type, the light beams strike the, e.g., spherically curved surface of the material at angles such that the light beams from the intact surface are not reflected into the reception device. According to the present invention, the type of curvature is not necessarily limited to a conic section. It can be adapted accordingly, optionally, by one skilled in the art, so that the light beams reflected on the flawless surface of the material do not strike the reception device. A concave mirror curved nearly 180° or a barrel-shaped mirror curved approximately in a semicircle can also be used.

According to the present invention, the light source can be easily positioned on an end face of the light strip, and a lamp of the light source is located in the normal plane of the scanning line in particular. As a result, an essentially radial illumination of the scanning line in an angular range of 180° is attained, which is quasi-diffuse.

To also attain a high level of illumination with these light components, two light sources are preferably located on each end face of the light strip in particular, the mirrors of which are optionally oriented such that they face each other.

A particularly great intensity is reached when the light source and/or the light strip include a discrete, high-intensity lamp.

To increase the contrast of the reception device when investigating transparent materials, it can be provided according to the present invention to position a light trap such that the pick-up area of the reception device points into the light trap. As a result, light reflectance from a scratch, which enters the reception device, is detected with a particularly high level of probability.

The, present invention also relates to the detection of scratches on a surface of a material, which can be carried out with the aforementioned device, in particular. With the method, the surface of the material is illuminated with an illumination device, and it is registered by a reception device along a specified scanning line. According to the present invention, the illumination device is positioned such that, when the surface of the material is flawless, no light from the illumination device enters the reception device. To increase the contrast, the reception device can look into a light trap when the surface of a transparent material is investigated. Diffuse or quasi-diffuse illumination takes place in two non-parallel—orthogonal in parlicular—directions, so that light components strike the surface in all spacial directions, and scratches can be detected with a high level of certainty.

According to the present invention, the illumination device preferably illuminates the surface of the material diffusely and/or quasi-diffusely with a scattering angle of nearly 180°.

In an advantageous embodiment of the method, the position of a flaw in the surface of the material is identified, and the length, form, and/or direction of a scratch are determined. This information is important in order to identify the cause of the scratch, and to eliminate it.

When the scratches are continuous, it is relatively easy to determine their length. Some scratches are discontinuous, due to their cause. To detect discontinuous scratches, it can be provided, according to the present invention, that new scratches are looked for at the end of a scratch at a specified angle and along a specified path. Discontinuous scratches can also be located using a search algorithm of this type, however. A direct relationship between scratches can also be attained, e.g., by performing a directional analysis of the scratch segments. When several scratch segments are located on a continuous path, it can be assumed that they have the same cause.

To show the scratches, they can be depicted on a display, in a printout, or the like. It is also possible to depict several scratch segments such that they are recognizable as being connected.

Further features, advantages, and possible applications of the present invention also result from the following description of exemplary embodiments and the drawing. All of the described and/or graphically depicted features are part of the present invention, either alone or in any combination, independently of their wording in the claims or their back-references.

DETAILED DESCRIPTION OF THE PREFERRED EMBODIMENTS

Figure 1:
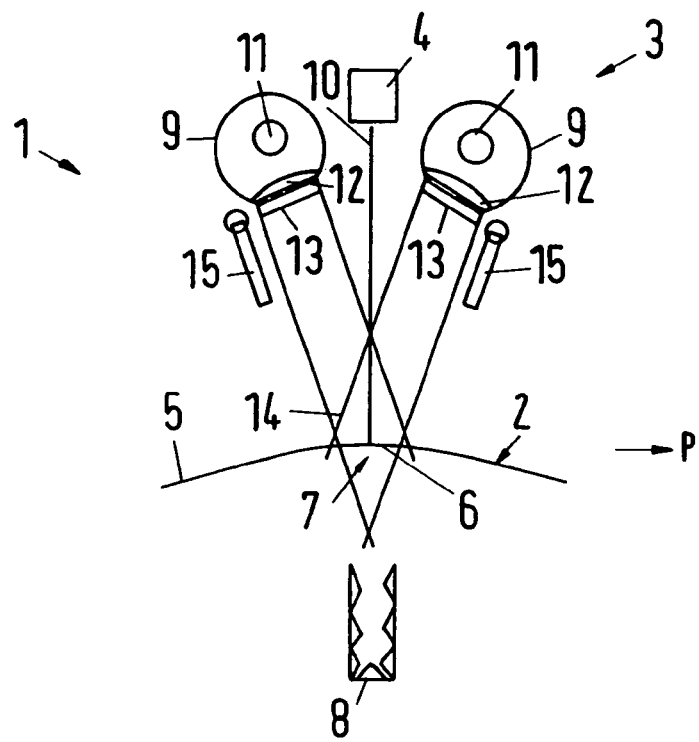
FIG. 1 shows a horizontal cross-section through a device for detecting scratches according to a first embodiment of the present invention.

Device 1—which is depicted schematically in FIG. 1—for detecting scratches on a surface 2 of a material includes an illumination device 3 and a reception device 4 in the form of a digital camera, which is oriented toward surface 2 of a windshield 5, where it covers a scanning line 6 which extends transversely to the cross-section of the illustration, along the entire height of the pane. When scanning line 6 would not extend along the entire height of the pane, it would be feasible to move device 1 with illumination device 3 and reception device 4 and/or windshield 5 along scanning line 6. The design shown is preferred, however, in which stationary reception device 4 covers scanning line 6 with its pick-up area 7 across the entire height of the pane, and windshield 5 is moved transversely to the pick-up direction, to scan entire surface 2 of windshield 5.

A light trap 8 is shown on the side of windshield 5 opposite to reception device 4, into which reception device 4 (camera) looks.

In order to detect scratches on surface 2 of the material, it must be illuminated with diffuse or quasi-diffuse light with an incident angle range of approximately 180° in the region of scanning line 6, which is registered by reception device 4, so that light reflectance from the scratch is also reflected into reception device 4 with a high level of certainty.

To this end, scanning line 6 is illuminated from the side by illumination device 3. This lateral illumination is provided by two straight, essentially perpendicular light strips 9, which are tilted toward each other. Camera 4 is located between light strips 9, essentially in the region of surface normal 10 of a point on scanning line 6. When windshield 5 is moved via a translatory motion in the direction of arrow P relative to device 1, the direction of surface normal 10 changes due to the spherical curvature of windshield 5. In this case, camera 4 is located, according to the present invention, in the region of surface normal 10, when it is located nearly in the center of the area covered by surface normal 10 in the vertical and/or horizontal direction.

Discrete, high-intensity lamps 11 are installed in light strips 9. Lamps 11 are needed for high luminosity. The light beams exit in parallel through optics. A lenticular system 13 is installed behind optics 12 to blend the exiting light. Lenticular system 13 is composed of microcylinder lenses, which distribute the light uniformly, with high transparency. If a matt screen were used instead of lenticular system 13, transmission losses would result. In this manner, the light in the vertical direction is absolutely diffuse. This facilitates the illumination—described below—of scratches from above and below, without light being reflected into camera 4, as would be the case with an intact material surface 2. Light strips 9 therefore each generate light which is parallel transversely to scanning line 6 and is diffuse along scanning line 6.

Via the design depicted in FIG. 1, uniform illumination from two sides of scanning line 6 at a certain depth is attained in region 14. The depth should be as great as the rise of the arch of windshield 5.

Flaps 15 are installed on the side of each light strip 9, which can be folded in front of optics 12 with lenticular system 13 of light strips 9 when there is a risk of direct reflectance reaching camera 4. The electrical switching of high-intensity lamps 11 is often not rapid enough; it is therefore easier to temporarily cover one lamp. Even when a lamp 11 must be covered by flaps 15, illumination still covers 180°, thereby ensuring that all scratches can be seen.

Figure 2:
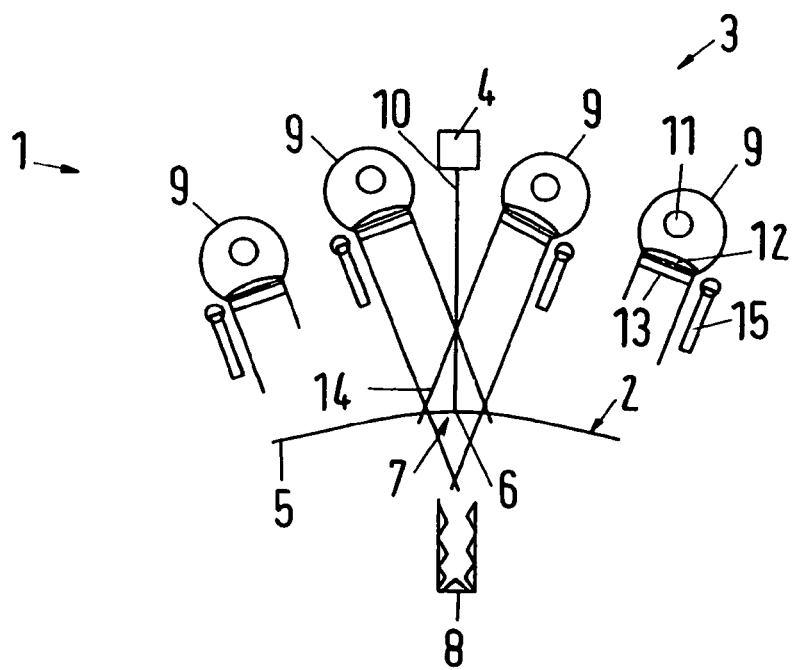
FIG. 2 shows a horizontal cross-section through a device for detecting scratches according to a second embodiment of the present invention.

FIG. 2 shows a design similar to FIG. 1, in which two light strips 9 are located on each side of the reception device. The design of each light strip 9 and the remainder of device 1 are identical; it will therefore not be described in detail here. A design of this type is recommended for use with sharply curved panes, in particular. According to the present invention, it is possible for light strips 9 to be switched separately. It is also possible, according to the present invention, to design light strips 9 such that they are displaceble, transversely to scanning line 6 in particular, to orient the parallel light beams, e.g., by rotating light strip 9 around its own axis, toward the pick-up area of reception device 4. It is also possible, according to the present invention, to adjust the distance from light strips 9 to surface 2 of the material together or separately. This also applies for further light sources 16, which shall be described in greater detail below with reference to FIGS. 3 and 4.

Figure 3:
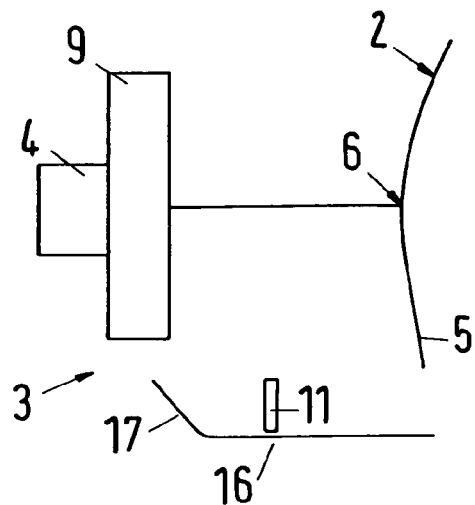
FIG. 3 shows a vertical partial cross-section through the device according to FIG. 1, with a light source.

To illuminate windshield 5 from above and below, a light source 16 is located at each of the end faces of light strips 9, only one of which is shown in FIG. 3. Light source 16 also includes a high-intensity lamp 11. Lamp 11 is located on the interior side of a mirror 17, which is designed as a conic section and is preferably provided with a not-shown shield against direct illumination of windshield 5. A shield of this type is not necessary for the inventive principle, however.

As shown in FIG. 3, mirror 17 has a straight back side, which is tilted—in accordance with a conic section—and curves by approximately 180°. From this mirror 17, light beams reflected by lamp 11 strike spherical windshield 5 quasi-diffusely, where they are reflected by an intact surface 2 such that no disturbing reflectances strike a camera 4 located in the region of surface normal 10 of a point on scanning line 6. The shape of the mirror also facilitates vertically diffuse illumination. Only the lower light source 16 is shown in FIG. 3. Top light source 16 has the same design, and is mirrored around the middle plane, thereby resulting in a nearly barrel-shaped design overall.

Figure 4:
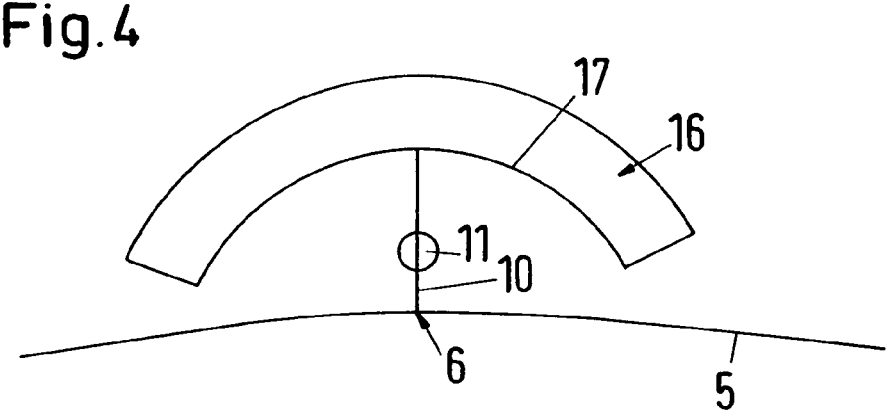
FIG. 4 shows a horizontal cross-section through the light source according to FIG. 3.

Quasi-diffuse light is generated transversely to scanning line 6 by the fact that conical mirror 17 is guided around the vertical line of scanning line 6 along a certain length, as shown in FIG. 4. Lamp 11 is located in the normal plane of scanning line 6 such that light strikes windshield 5 within an angular range of approximately 180°. The lamp is located in the center of curvature of mirror 17. To obtain other illumination angles, several lamps 11 can be located, one after the other, along surface normal 10 in particular. It is even possible, in principle, to replace mirror 17 with lamps 11 which are positioned accordingly, to generate the quasi-diffuse light.

Via illumination device 3 with light strips 9 and light sources 16, diffuse and/or quasi-diffuse light is generated on surface 2 of a spherically curved pane 5 at an adequate depth range with two directions which are essentially orthogonal to each other within an angular range of 180°, so that pane 5 is illuminated adequately to detect all possible scratches. It is also possible to use device 1 to inspect planar glass for scratches, of course.

Device 1 described above operates using reflectance, i.e., camera 4 and illumination device 3 are located on the same side. Device 1 with inventive illumination device 3 can also be designed such that it operates via transmission. In this case, camera 4 and illumination device 3 are located on different sides of transparent surface 2 of the material.

When light reflectance is detected in camera 4 of device 1, this indicates the presence of a flaw in material surface 2. With a not-shown evaluation unit connected to device 1, the position of the flaw on surface 2 of the material is identified, and the length, form, and/or direction of a scratch 18 are determined.

Figure 5:
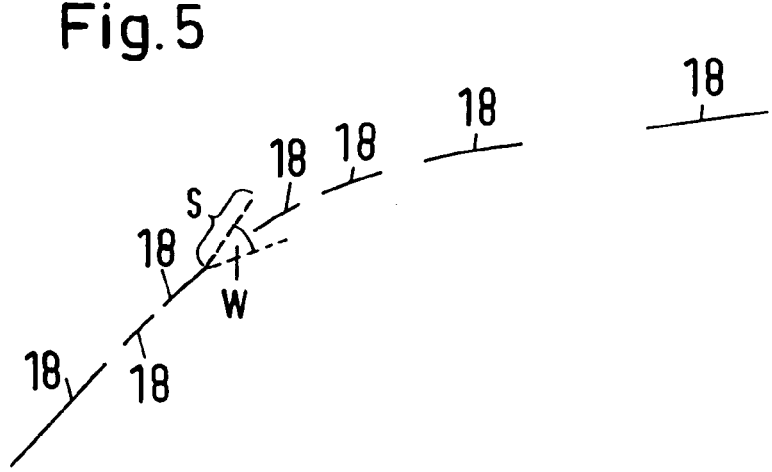
FIG. 5 shows a scratch on the surface of the material to be investigated.

It is easy to determine the length of the scratch when scratches 18 are continuous. Some scratches 18 are discontinuous, however, due to their cause. The cause of these scratch tracks is easier to determine the more thoroughly scratch 18 can be followed. The fact that the discontinuous scratch tracks are usually located on the same path can usually be determined very well with the human eye. When this is carried out by a machine, a search algorithm must be used. This algorithm will be explained below with reference to FIG. 5.

Tracks of new scratches 18 are looked for from the end of a scratch segment 18 at a certain angle W and along a certain path S having a specifiable length. If new scratches 18 are found in this area, this indicates that is a continuing scratch 18. The search is continued at the end of the next scratch segment 18, until no new scratches 18 are found in the search area. The angle W and path S for the search area can be adjusted based on individual perspectives.

The result of the scratch detection is depicted by the evaluation device in a manner known per se. With this method, and when using device 1 in particular, a scratch 18 can be found anywhere on material surface 2 with a high degree of certainty.

REFERENCE NUMERALS

1 Device for detecting scratches
2 Material surface
3 Illumination device
4 Reception device
5 Windshield
6 Scanning line
7 Pick-up area
8 Light trap
9 Light strip
10 Surface normal
11 High-intensity lamp
12 Optics
13 Lenticular system
14 Area
15 Flap
16 Light source
17 Mirror
18 Scratch
P Arrow
W Angle
S Path What claimed is:

1. A device for detecting scratches on a surface (2) of a material, in particular glass, said device comprising an illumination device (3) for illuminating the surface of the material and a reception device (4), which detect a scanning line (6) on the surface (2) of the material and which are displaceable relative to the surface (2) of the material; and
   wherein the illumination device (3) includes at least one light strip (9), which generates parallel light transversely to the scanning line (6), and at least one light source (16), which generates diffuse or quasi-diffuse light transversely to the scanning line (6), and
   wherein the at least one light source (16) is located on a respective end face of the at least one light strip (9), and the at least one light source (16) has at least one lamp (11) located in a normal plane of the scanning line (6).

2. The device as recited in claim 1, wherein the reception device (4) is located in the vicinity of a surface normal (10) of a point on the scanning line (6).

3. The device as recited in claim 1, wherein the at least one light strip (9) is positioned so that a region around the scanning line (6) is illuminated.

4. The device as recited in claim 1, wherein the light strip (9) includes optics (12) which orient light beams from the at least one light strip in parallel.

5. The device as recited in claim 1, wherein the light strip (9) includes a diffuser comprising a lenticular system (13), for generating the diffuse light in the direction of the scanning line (6).

6. The device as recited in claim 2, wherein two light strips (9) are provided, which are located on opposite sides of the surface normal (10).

7. The device as recited in claim 1, further comprising a flap (15) for covering the light strip (9) located on the light strip (9).

8. The device as recited in claim 1, wherein the light source (16) includes a curved mirror (17).

9. The device as recited in claim 8, wherein at least portions of the mirror (17) are conical.

10. The device as recited in claim 1, wherein two light sources (16) are provided and located on respective opposite end faces of the light strip (9).

11. The device as recited in claim 1, wherein the light strip (9) includes at least one high-intensity lamp (11).

12. The device as recited in claim 1, further comprising a light trap (8) positioned such that a pick-up region (7) of the reception device (4) points into the light trap (8).

13. A method of detecting scratches on a surface (2) of a material with a scratch detecting device, wherein said scratch detecting device comprises an illumination device (3) for illuminating the surface of the material and a reception device (4), which detect a scanning line (6) on the surface (2) of the material and which are displaceable relative to the surface (2) of the material, the illumination device (3) including at least one light strip (9) for generating parallel light transversely to the scanning line (6) and at least one light source (16) for generating diffuse or quasi-diffuse light transversely to the scanning line (6), the at least one light source (16) being located on a respective end face of the at least one light strip (9) and the at least one light source (16) having at least one lamp (11) located in a normal plane of the scanning line (6), said method comprising the steps of:

a) illuminating the surface (2) of the material with said illumination device (3), which is arranged so that the surface (2) of the material is illuminated with said diffuse or said quasi-diffuse light from two non-parallel directions;

b) positioning said illumination device (3) so that no light from the illumination device (3) enters the reception device (4) when the surface (2) of the material is flawless; and c) detecting the surface (2) of the material along a scanning line (6) with said reception device (4).

14. The method as recited in claim 13, wherein a position of a flaw in the surface (2) of the material is determined, and a length, form, and/or direction of a scratch (18) are determined.

15. The method as recited in claim 14, wherein new scratches (18) are looked for at the end of a scratch (18) at a specified angle (W) and on a specified path (S).

16. The method as recited in claim 13, wherein the illumination device (3) illuminates the surface (2) of the material diffusely and/or quasi-diffusely with a scattering angle of at least 180°.

* * * * *